(12) United States Patent
Schulman et al.

(10) Patent No.: US 6,821,462 B2
(45) Date of Patent: Nov. 23, 2004

(54) MASS PRODUCTION OF SHELLS AND MODELS FOR DENTAL RESTORATIONS PRODUCED BY SOLID FREE-FORM FABRICATION METHODS

(75) Inventors: Martin L. Schulman, Orange, CT (US); Carlino Panzera, Hillsborough, NJ (US)

(73) Assignee: Jeneric/Pentron, Inc., Wallingford, CT (US)

( * ) Notice: Subject to any disclaimer, the term of this patent is extended or adjusted under 35 U.S.C. 154(b) by 130 days.

(21) Appl. No.: 09/946,413

(22) Filed: Sep. 5, 2001

(65) Prior Publication Data

US 2002/0064745 A1 May 30, 2002

Related U.S. Application Data

(63) Continuation-in-part of application No. 09/350,604, filed on Jul. 9, 1999, now Pat. No. 6,322,728.
(60) Provisional application No. 60/092,432, filed on Jul. 10, 1998.

(51) Int. Cl.$^7$ .................. A61C 13/00; A61C 13/08; B29C 33/40; B29C 35/08; B29C 41/02
(52) U.S. Cl. ................ 264/16; 164/34; 264/17; 264/19; 264/221; 264/227; 264/308; 264/401; 264/497
(58) Field of Search ................ 264/16, 17, 19, 264/221, 227, 308, 401, 497; 164/34

(56) References Cited

U.S. PATENT DOCUMENTS

| | | |
|---|---|---|
| 3,066,112 A | 11/1962 | Bowen |
| 3,179,623 A | 4/1965 | Bowen |
| 3,194,784 A | 7/1965 | Bowen |
| 3,751,399 A | 8/1973 | Lee et al. |
| 3,926,906 A | 12/1975 | Lee, II et al. |
| 4,115,487 A | 9/1978 | Rockett et al. |
| 4,433,959 A | 2/1984 | Faunce |
| 4,544,359 A | 10/1985 | Waknine |
| 4,547,327 A | 10/1985 | Bruins et al. |
| 4,547,531 A | 10/1985 | Waknine |
| 4,575,805 A | 3/1986 | Moermann et al. |
| 4,663,720 A | 5/1987 | Duret et al. |
| 4,672,032 A | 6/1987 | Slavkin et al. |
| 4,717,341 A | 1/1988 | Goldberg et al. |
| 4,789,649 A | 12/1988 | Abert et al. |
| 4,894,012 A | 1/1990 | Goldberg et al. |
| 4,937,928 A | 7/1990 | van der Zel |
| 5,022,583 A | 6/1991 | Bruens |
| 5,104,319 A | 4/1992 | Evans et al. |
| 5,176,188 A * | 1/1993 | Quinn et al. ............ 164/516 |
| 5,204,055 A | 4/1993 | Sachs et al. |
| 5,276,068 A | 1/1994 | Waknine |
| 5,340,656 A | 8/1994 | Sachs et al. |
| 5,346,397 A | 9/1994 | Braiman |
| 5,387,380 A | 2/1995 | Cima et al. |
| 5,444,104 A | 8/1995 | Waknine |
| 5,490,882 A | 2/1996 | Sachs et al. |
| 5,490,962 A | 2/1996 | Cima et al. |
| 5,518,680 A | 5/1996 | Cima et al. |
| 5,587,913 A | 12/1996 | Abrams et al. |
| 5,679,144 A | 10/1997 | Thiel et al. |
| 5,684,103 A | 11/1997 | Jia et al. |
| 5,700,289 A | 12/1997 | Breitbart et al. |
| 5,900,207 A | 5/1999 | Danforth et al. |
| 5,910,273 A | 6/1999 | Thiel et al. |
| 5,969,000 A | 10/1999 | Yang et al. |
| 5,989,031 A | 11/1999 | Kura et al. |
| 6,013,694 A | 1/2000 | Jia et al. |
| 6,039,569 A | 3/2000 | Prasad et al. |
| 6,186,790 B1 | 2/2001 | Karmaker |
| 6,322,728 B1 | 11/2001 | Brodkin et al. |
| 6,354,836 B1 | 3/2002 | Panzera et al. |
| 2002/0033548 A1 | 3/2002 | Brodkin et al. |
| 2002/0125592 A1 | 9/2002 | Schulman et al. |

* cited by examiner

*Primary Examiner*—Leo B. Tentoni
(74) *Attorney, Agent, or Firm*—Ann M. Knab (57) ABSTRACT

Solid free form fabrication techniques such as fused deposition modeling and three-dimensional printing are used to create a shell used in the manufacture of a dental restoration. Three-dimensional printing includes ink-jet printing a binder into selected areas of sequentially deposited layers of powder. Each layer is created by spreading a thin layer of powder over the surface of a powder bed. Instructions for each layer may be derived directly from a CAD representation of the restoration. The area to be printed is obtained by computing the area of intersection between the desired plane and the CAD representation of the object. All the layers required for an aesthetically sound shell can be deposited concurrently slice after slice and sintered/cured simultaneously. While the layers become hardened or at least partially hardened as each of the layers is laid down, once the desired final shaped configuration is achieved and the layering process is complete, in some applications it may be desirable that the form and its contents be heated, cooled or cured at a suitably selected temperature to further promote the integrity of solid free-form structures.

10 Claims, 3 Drawing Sheets

MASS PRODUCTION OF SHELLS AND MODELS FOR DENTAL RESTORATIONS PRODUCED BY SOLID FREE-FORM FABRICATION METHODS

CROSS-REFERENCE TO RELATED APPLICATIONS

This application is a continuation-in-part of U.S. application Ser. No. 09/350,604 filed Jul. 9, 1999, now U.S. Pat. No. 6,322,728, which claims priority to U.S. Provisional Application Ser. No. 60/092,432 filed on Jul. 10, 1998, both which are hereby incorporated by reference.

FIELD OF THE INVENTION

This invention relates to dental restorations made from ceramics, glass-ceramics as well as ceramic-matrix and polymer-matrix composite materials using solid free-form fabrication methods. The invention further relates to bodies fabricated by solid free-form techniques which can provide the matrix or skeleton of dental restorations that can be further or concurrently filled with biomimetic substances. The invention also is directed to the manufacture of shells used in the manufacture of dental restorations whereby the shells are manufactured using solid free-form fabrication methods. The invention further relates to the manufacture of models used in the manufacture of dental restorations whereby the models are manufactured using solid free-form fabrication methods.

BACKGROUND OF THE INVENTION

The fabrication of current all-ceramic dental restorations often requires extensive labor and time and the proficiency of highly skilled technicians. Many state-of-the-art dental restorations reveal a sense of artistry that can typically only be achieved manually or "by hand." While aesthetics are preserved with this process, microstructural inhomogeneities may appear, affecting strength and reliability. The industry has attempted to automate this process by, for example, pressing crowns. Although pressable crowns reduce some of the skill time required, about two hours of concerted effort is necessary to complete a crown. Pressed crowns may also suffer from similar strength and reliability problems typical of "hand made" crowns.

Computer assisted design/computer assisted milling (CAD/CAM) processes and equipment have been recently introduced into the dental industry. In these processes, a three-dimensional image of a tooth to be restored is created along with the teeth surrounding the tooth in an effort to create a dental restoration which is to be placed over the tooth. This image is displayed on a computer screen. Based on the tooth and surrounding teeth, the dental technician may then select a tooth from a plurality of tooth forms stored in the computer to best fit the tooth to be restored. The selected tooth is projected onto the tooth to be restored until an optimum positioning and fit of the dental restoration is achieved. The digital data concerning the dental restoration thus formed are supplied to a numerically controlled milling machine operating in three dimensions. The milling machine cuts a blank of metal or porcelain material into the dental restoration design based on the data supplied.

Commercially available systems such as CEREC™ from Siemens, PROCERA® from Nobel Biocare AG, and CICERO® from Cicero Dental Systems, have attempted to reduce labor and increase structural reliability. However, the necessary machining steps limit the choice of materials that can be used in dental restorations and sometimes compromise the strength and/or aesthetics of the finished restoration.

One of the current limitations of the CAD/CAM approach, which is not easy to overcome, is the fact that currently available systems at best produce copings that require veneering layers to provide a natural appearance. Consequently, final processing of the crown is still in the hands of dental technicians which may limit the resulting structural reliability of the restoration. The existing commercial CAD/CAM systems are unable to produce full crowns. Some of the systems can machine inlays/onlays from a solid ceramic block and are not able to produce crowns or even copings. Others produce copings that make a core of the crown that can fit on the prepared tooth but require additional work by dental technicians to provide final shapes and esthetics. This entails manual building and firing of porcelain layers on top of a coping received from the CAD/CAM facility. Supposedly, one or more systems will be able to automate forming of successive veneering layers of porcelain on top of a CAD/CAM coping which will involve sintering of consecutive porcelain layers following their forming by machining or pressing. This is an automation of steps that are otherwise performed by dental technicians and very well may not be practically advantageous.

One of the key limitations intrinsic to CAM methods is the fact that machining is not competitive technology for mass production of parts and components of any kind including dental restorations, e.g. dentures and crowns. At any given period of time one cutting tool can be used to machine only one part and can not be concurrently used to machine another part.

It is desirable that the automation of the manufacture of dental restorations be conducive to mass production of restorations. It is beneficial that the automation of the manufacture of dental restorations be efficient and useful for a variety of materials.

SUMMARY OF THE INVENTION

These and other objects and advantages are accomplished by the process herein directed to solid free-form (SFF) fabrication of dental restorations. Among solid free-form techniques, dimensional printing and fused deposition modeling are preferred because both ceramic and resin-based composite dental restorations can be produced in solid (e.g. denture teeth) or multilayered form (e.g. crowns). Three-dimensional printing is most preferred for mass-production of dental restorations.

Three-dimensional printing is used to create a dental restoration by ink-jet printing a binder into selected areas of sequentially deposited layers of powder. Each layer is created by spreading a thin layer of powder over the surface of a powder bed. Instructions for each layer may be derived directly from a CAD representation of the restoration. The area to be printed is obtained by computing the area of intersection between the desired plane and the CAD representation of the object. All the layers required for an aesthetically sound restoration can be deposited concurrently slice after slice and sintered/cured simultaneously. The amount of green body oversize is equivalent to the amount of shrinkage which occurs during sintering or curing. While the layers become hardened or at least partially hardened as each of the layers is laid down, once the desired final shaped configuration is achieved and the layering process is complete, in some applications it may be desirable that the form and its contents be heated or cured at a suitably selected temperature to further promote binding of the powder particles. The individual sliced segments or layers are joined by one or more binders to form the three dimensional structure. The unbound powder supports temporarily unconnected portions of the component as the structure is built but is removed after completion of printing.

BRIEF DESCRIPTION OF THE DRAWINGS

Features of the present invention are disclosed in the accompanying drawings, wherein similar reference characters denote similar elements throughout the several views, and wherein.

DESCRIPTION OF THE INVENTION

A number of techniques have been developed in recent years that are known under the generic name of solid free-form (SFF) fabrication or also known as rapid prototyping and are successfully used for net-shape manufacturing of advanced materials (ceramics, polymers) into small and complex shapes. These techniques are similar to CAD/CAM techniques in that the digital representation of the final shape and its implementation is designed and controlled by a computer. However, the machining step in these techniques is substituted by other computer assisted net-shaping techniques including but not limited to three-dimensional printing, selective area laser deposition or selective laser sintering (SLS), electrophoretic deposition, robocasting, fused deposition modeling (FMD), laminated object manufacturing (LOM), stereolithography and photostereolithography. Most of these techniques were developed for net-shaped fabrication of polymeric or wax parts, however, some of them, such as three-dimensional printing and fused deposition modeling can be used to build complex shapes from ceramic or even metallic materials as well. A large variety of ceramic, polymeric and composite materials can be fabricated into complex shapes using these techniques. U.S. Pat. Nos. 5,340,656, 5,490,882, 5,204,055, 5,518,680, 5,490,962, 5,387,380, 5,700,289, 5,518,680, and 4,672,032 are directed to solid free-form fabrication methods and techniques and are hereby incorporated by reference.

In this invention, solid free-form techniques are used to make dental restorations including but not limited to denture teeth, bridges, crowns, bridges, space maintainers, tooth replacement appliances, orthodontic retainers, dentures, posts, jackets, inlays, onlays, facings, veneers, facets, implants, abutments, splints, partial crowns, teeth, cylinders, pins, and connectors. Among solid free-form techniques, dimensional printing and fused deposition w modeling are preferred because both ceramic and resin-based composite dental restorations can be produced in solid (e.g. denture teeth) or multilayered form (e.g. crowns). Three-dimensional printing is most preferred for mass-production of dental restorations.

Similarly to CAD/CAM methods, the design of the restoration is carried by a CAD device which uses at least two inputs: (1) the digital image taken optically directly from a mouth of the patient (optical impression) or created by digitizing the impression/die by contact or by an optical digitizer; and (2) a library of teeth shapes and forms. CAD devices assure both natural-like shape and proper function of the restoration. Both optical and contact digitizers providing input (1) above are described in the literature and some of them are commercially available. The specific techniques may require additional software to build the shape according to the CAD file.

In one of the embodiments of the present invention, a three-dimensional printing machine is used for mass-production of dental restorations including, but not limited to denture teeth, bridges, crowns, bridges, space maintainers, tooth replacement appliances, orthodontic retainers, dentures, posts, jackets, inlays, onlays, facings, veneers, facets, implants, abutments, splints, partial crowns, teeth, cylinders, pins, and connectors. Suitable printing devices include both those with a continuous jet stream print head and a drop-on-demand stream print head. A high speed printer of the continuous type may be used which has a line printing bar containing approximately 1500 jets which can deliver up to 60 million droplets per second in a continuous fashion and can print at speeds up to 900 feet per minute. Both raster and vector apparatuses can be used. A raster apparatus is where the printhead goes back and forth across the bed with the jet turning on and off. This can have problems when the material is likely to clog the jet upon settling. A vector apparatus is similar to an x-y printer. Although potentially slower, the vector printer may yield a more uniform finish.

Three-dimensional printing is used to create a dental restoration by ink-jet printing a binder into selected areas of sequentially deposited layers of powder. Each layer is created by spreading a thin layer of powder over the surface of a powder bed. The powder bed is supported by a piston which descends upon powder spreading and printing of each layer, or conversely, the ink jets and spreader are raised after printing of each layer and the bed remains stationary. Instructions for each layer may be derived directly from a CAD representation of the restoration. The area to be printed is obtained by computing the area of intersection between the desired plane and the CAD representation of the object. The individual sliced segments or layers are joined to form the three dimensional structure. The unbound powder supports temporarily unconnected portions of the component as the structure is built but is removed after completion of printing.

The three-dimensional printing apparatus includes a powder dispersion head which is driven reciprocally in a shuttle motion along the length of the powder bed. A linear stepping motor assembly is used to move the powder distribution head and the binder deposition head. The powder material is dispensed in a confined region as the dispensing head is moved in discrete steps along the mold length to form a relatively loose layer having a typical thickness of about 100 to about 200 microns. All the layers required for an aesthetically sound restoration can be deposited concurrently slice after slice and sintered/cured simultaneously. The amount of green body oversize is equivalent to the amount of shrinkage which occurs during sintering or curing. Although powder is used herein to identify the material, the material may include particles of any shape including fibers, rod-shaped particles, spherical particles, or any shape or form of material used in the manufacture of dental restorations. An ink jet print head having a plurality of ink-jet dispensers is also driven by the stepping motor assembly in the same reciprocal manner so as to follow the motion of the powder head and to selectively produce jets of a liquid binder material at selected regions thereby causing the powdered material at such regions to become bonded. The binder jets are dispensed along a line of the printhead which is moved in substantially the same manner as the dispensing head. Typical binder droplet sizes are about 15 to about 50 microns. The powder/binder layer forming process is repeated so as to build up the restoration, layer by layer.

While the layers become hardened or at least partially hardened as each of the layers is laid down, once the desired final shaped configuration is achieved and the layering process is complete, in some applications it may be desirable that the form and its contents be heated or cured at a suitably selected temperature to further promote binding of the powder particles. In either case, whether or not further curing is required, the loose, unbounded powder particles are removed using a suitable technique, such as ultrasonic cleaning, to leave a finished restoration.

For effective use, the powder particles should be uniformly deposited at a relatively high rate, the rate being selected in accordance with the application for which the technique is used. For many useful applications the powder particles can preferably be packed at relatively high densities, while in other applications the density may be considerably lower where restorations having greater porosity are desired. Known techniques used in the fields of colloidal science and powder dispersion chemistry can be used to provide the desired uniform depositions of such powders at the required rates and densities. Thus, powders can be dispensed either as dry powders or in a liquid vehicle, such as in a colloidal dispersant or in an aqueous suspension. In the dry state, the desired compaction of particles can be achieved using mechanical vibrating compaction techniques or by applying acoustic energy, i.e., either sonic or ultrasonic vibrations, to the deposited powder or by applying a piezoelectric scraper to the deposited powder.

The ink-jet printing of the binder material should utilize droplets of materials having shrinkage characteristics such that the dimensional tolerances of the restoration being made are maintained upon hardening thereof. While the binder solution must have a relatively high binder content, the viscosity thereof should be low enough so as to be able to flow through the printing head for deposit into the powder material. The binder material should be selected to penetrate the layer and to perform its binding action relatively rapidly in each layer so that the next layer of powder particles can be subsequently applied thereto. When using certain ink-jet technology the binder material may require at least a minimum electrical conductivity, particularly when using currently available continuous jet printing heads, for example, which require enough conductivity to establish charge on the binder solution droplets as they are emitted from the head. Where conductivity cannot be established in the binder, as with certain organic solvents, for example, the binder can be applied using drop-on-demand print heads.

The binder material may have a high binding strength as each layer is deposited so that, when all the layers have been bonded, the component formed thereby is ready for use without further processing. In other cases, it may be desirable, or necessary, to perform further processing of the restoration. For example, while the process may be such as to impart a reasonable strength to the restoration which is formed, once the restoration is formed it can be further heated or cured to further enhance the binding strength of the particles. In some cases, the binder is removed during such heating or firing process, while in others, it can remain in the material after firing. Which operation occurs depends on the particular binder material which has been selected for use and on the conditions, e.g., temperature, under which the heating or firing process is performed. Other post-processing operations may also be performed following the formation of the restoration. The rate at which a ceramic, metal, plastic, or composite restoration can be made depends on the rates used to deposit the powder and to supply the binder liquid, and on the rate at which each bonded layer hardens as the layers are deposited one on the other.

Alumina, zirconia, mullite, silica, spinel, tricalcium phosphate, apatite, fluoroapatite, hydroxyapatite and mixtures thereof are representative ceramic materials which can be used in the solid free form fabrication techniques of the invention to form dental restorations. To enhance sintering, particles can be coated with silica, for example by treating with TEOS as described below. Many possible combinations of powder and binder materials can be selected in accordance with the invention. For example, ceramic powders or ceramic fibers can be used with either inorganic or organic binder materials or with a metallic binder material; a metal powder can be used with a metallic binder or a ceramic binder; and a plastic powder can be used with a solvent binder or a plastic binder, e.g., a low viscosity epoxy plastic material. Other appropriate combinations of powder and binder materials will occur to those in the art for various applications.

The resulting color including but not limited to shade, translucency, and fluorescence, of the restoration is controlled by the pigments, opacifiers, fluorescing agents and the like, added to the powder bed components as well as components delivered through nozzles. The printed material that is used to bond successive layers can be a curable or removable organic material. When a curable material is used, the polymer-ceramic composite restoration results from the green body after curing is completed. Both natural and synthetic dispersants are available for these materials in organic vehicles. Organic dispersants have been used in the ceramics industry and are typically polymeric resins obtained form a variety of sources. They can be either water soluble, such as cellulosic binders, as used in extrusion technology, or they can be soluble in only volatile organic solvents, such as the butyral resins, as used in tape casting technology. The latter water soluble systems can be removed relatively quickly and seem particularly useful in the invention. Another example of a binder is a ceramic precursor material such as polycarbosilazane.

Inorganic binders are useful in cases where the binder is to incorporated into the final component. Such binders are generally silicate based and are typically formed from the polymerization of silicic acid or its salts in aqueous solution. An exemplary inorganic binder which can be used is tetraethylorthosilicate (TEOS). During drying, the colloidal silica aggregates at the necks of the matrix particles to form a cement-like bond. During firing, the silica flows and acts to rearrange the matrix particles through the action of surface tension forces and remains after firing.

Composite materials for use in the invention include a polymeric matrix with particulate or fiber filled components. The polymeric matrix element of the fiber-reinforced and particulate-filled composites is selected from those known in the art of dental materials, including but not being limited to polyamides, polyesters, polyolefins, polyimides, polyarylates, polyurethanes, vinyl esters or epoxy-based materials. Other polymeric matrices include styrenes, styrene acrylonitriles, ABS polymers, polysulfones, polyacetals, polycarbonates, polyphenylene sulfides, and the like.

Preferred polymeric materials include those based on acrylic and methacrylic monomers, for example those disclosed in U.S. Pat. Nos. 3,066,112, 3,179,623, and 3,194,784 to Bowen; U.S. Pat. Nos. 3,751,399 and 3,926,906 to Lee et al.; commonly assigned U.S. Pat. Nos. 5,276,068 and 5,444,104 to Waknine; and commonly assigned U.S. Pat. No. 5,684,103 to Jia et al., the pertinent portions of all which are herein incorporated by reference. An especially preferred methacrylate monomer is the condensation product of bisphenol A and glycidyl methacrylate, 2,2'-bis[4-(3-methacryloxy2-hydroxy propoxy)-phenyl]-propane (hereinafter abbreviated "BIS-GMA"). Polyurethane dimethacrylates (hereinafter abbreviated "PUDMA"), triethylene glycol dimethacrylate (hereinafter abbreviated "TEGDMA"), polyethylene glycol dimethacrylate (hereinafter abbreviated "PEGDMA"), polycarbonate dimethacrylate (hereinafter abbreviated "PCDMA") and ethoxylated bisphenol A dimethacrylate (hereinafter abbreviated "EBPADMA") are also commonly-used principal polymers suitable for use in the present invention.

The polymer matrix typically includes polymerization initiators, polymerization accelerators, ultraviolet light absorbers, anti-oxidants, and other additives well known in the art. The polymer matrices may be visible light curable, self-curing, dual curing, and vacuum, heat, and pressure curable compositions as well as any combination thereof. The visible light curable compositions include the usual polymerization initiators, polymerization accelerators, ultraviolet absorbers, fluorescent whitening agents, and the like. Preferred light curing initiators include camphorquinone (CQ) and trimethyl benzoyl phosphine oxide (TPO). The heat curable compositions, which are generally filled compositions, include, in addition to the monomeric components, a heat cure initiator such as benzoyl peroxide, 1,1'-azobis(cyclohexanecarbo-nitrile), or other free radical initiators. The preferred fiber-reinforced polymeric matrix is a curable matrix, wherein light cure effects partial cure of the matrix, and final curing is by heat under controlled atmosphere.

The fiber-reinforced polymeric matrix may further comprise at least one filler known in the art and used in dental restorative materials, the amount of such filler being determined by the specific use of the fiber-reinforced composite. Generally, no or relatively little additional filler is present in the polymeric matrix, i.e., up to thirty percent by weight of the composite. Suitable fillers are those capable of being covalently bonded to the polymeric matrix itself or to a coupling agent that is covalently bonded to both. Examples of suitable filling materials include but are not limited to those known in the art such as silica, silicate glass, quartz, barium silicate, strontium silicate, barium borosilicate, strontium borosilicate, borosilicate, lithium silicate, amorphous silica, ammoniated or deammoniated calcium phosphate and alumina, zirconia, tin oxide, and titania. Particularly suitable fillers for dental filling-type materials prepared in accordance with this invention are those having a particle size ranging from about 0.1–5.0 microns with a silicate colloid of 0.001 to about 0.07 microns and may be prepared by a series of milling steps comprising wet milling in an aqueous medium, surface etch milling and dry or wet silanation. Some of the aforementioned inorganic filling materials are disclosed in commonly-assigned U.S. Pat. Nos. 4,544,359 and No. 4,547,531 to Waknine, the pertinent portions of which are incorporated herein by reference.

The particulate-filled polymeric matrix comprises at least one filler known in the art and used in dental restorative materials, the amount of such filler being determined by the specific use of the particulate-filled composite. Generally, from about 65 to about 85% by weight of a filler is present in the particulate-filled composite and preferably, about 75 to about 83% by weight of the composite is filler in combination with about 17 to about 35% by weight and preferably about 20 to about 30% by weight and more preferably about 20 to about 26% by weight of the composite is unfilled heat curable dental resin material which makes up the polymeric matrix. Suitable fillers are those capable of being covalently bonded to the polymeric matrix itself or to a coupling agent that is covalently bonded to both.

Examples of suitable filling materials include but are not limited to those known in the art such as silica, silicate glass, quartz, barium silicate, barium sulfate, barium molybdate, barium methacrylate, barium yttrium alkoxy ($Ba_2Y(OR)_x$), strontium silicate, barium borosilicate, strontium borosilicate, borosilicate, lithium silicate, amorphous silica, ammoniated or deammoniated calcium phosphate, alumina, zirconia, tin oxide, tantalum oxide, niobium oxide, and titania. Particularly suitable fillers for dental filling-type materials prepared in accordance with this invention are those having a particle size ranging from about 0.1–5.0 microns with a silicate colloid of 0.001 to about 0.07 microns and may be prepared by a series of milling steps comprising wet milling in an aqueous medium, surface etch milling and dry or wet silanation. Some of the aforementioned inorganic filling materials are disclosed in commonly-assigned U.S. Pat. Nos. 4,544,359 and 4,547,531 to Waknine, the pertinent portions of which are incorporated herein by reference.

Preferably, the particulate-filled composite comprises an inorganic filler having an average particle size diameter of about 0.5 to about 5 microns homogeneously dispersed in an organic polymerizable monomeric matrix comprising ethoxylated dimethacrylate which is set forth in commonly owned, copending application Ser. No. 08/998,849 filed Dec. 29, 1997 which is hereby incorporated by reference. In addition, a relatively small amount of fumed silica is also predispersed within the monomeric matrix. The inorganic filler primarily comprises an X-ray opaque alkali metal or alkaline earth metal silicate such as lithium alumina silicate, barium silicate, strontium silicate, barium borosilicate, strontium silicate, barium borosilicate, strontium borosilicate, borosilicate, as well as the aforementioned materials. For purposes of illustration, and as the preferred silicate species, barium borosilicate will hereinafter be employed as being typical of the alkali metal or alkaline earth metal silicates which can be suitable employed in the present invention. The barium borosilicate exhibits an index of refraction close to that of the organic monomeric matrix in which it is dispersed. The filler can additionally contain a relatively small amount of borosilicate glass which imparts greater compressive strength to the resulting composite and enhances the translucency thereof thereby enabling better blending of the restorative material with the adjacent teeth. In addition, the presence of the borosilicate glass helps narrow the gap in the mismatch of refractive indices between the barium borosilicate inorganic fiber phase and the organic monomeric matrix.

Details of the preparation of the inorganic filler, which comprises a mixture of from about 5 to about 20% by weight of borosilicate glass and form about 80 to about 95% by weight barium borosilicate, and has an average particle size diameter of from about 0.5 to about 5 microns, can be found in the aforementioned U.S. Pat. Nos. 4,544,539 and 4,547,531.

The reinforcing fiber element of the fiber-reinforced composite preferably comprises ceramic, glass, carbon, graphite, polyaramid, or other fibers or whiskers known in the art, such as polyesters, polyamides, and other natural and synthetic materials compatible with the polymeric matrix. Some of the aforementioned fibrous materials are disclosed in commonly assigned copending U.S. patent application Ser. Nos. 08/907,177, 09/059,492, 60/055,590, 08/951,414 and U.S. Pat. Nos. 4,717,341 and 4,894,012 all which are incorporated herein by reference. The fibers may further be treated, for example, chemically or mechanically etched and/or silanized, to enhance the bond between the fibers and the polymeric matrix. The fibers preferably take the form of long, continuous filaments, although the filaments may be as short as 0.1 to 4 millimeters. Shorter fibers of uniform or random length might also be employed. Preferably, the fibers are at least partially aligned and oriented along the longitudinal dimensions of the wire. However, depending on the end use of the composite material, the fibers may also be otherwise oriented, including being normal or perpendicular to that dimension.

In some applications, it may be preferable that the binder harden relatively rapidly upon being deposited so that the next layer of particles placed on a surface of the previous layer is not subject to particle rearrangement due to capillary forces. Moreover, a hardened binder is not subject to contamination from solvents which may be used in powder deposition. In other cases, it may not be necessary that the binder be fully hardened between layers and a subsequent layer of powder particles may be deposited on a previous layer which is not yet fully hardened.

The number of restorations printed simultaneously is essentially limited by the size of the powder bed, number of nozzles and the ability to recognize and sort different restorations. To facilitate the latter operation, the robotized device can be used to pick up and sort different restorations.

It is an essential part of the present invention that components creating and/or modifying color, translucency, biocompatibility, mechanical properties (strength, fracture toughness and wear) and perceived shape are contained in the powder bed and/or delivered through nozzles. This offers a unique advantage in creating esthetics (colors, shapes) and structure (functionally gradient structures). Techniques similar to water-marks are used to create interference colors, opalescence and fluorescing effects. Other techniques are used to create perceived geometry similar to techniques used in sculpture to create impressions of the face that is perceived as a full-bodied face always looking at the observer from any angle of view.

In another embodiment of the present invention, moldable articles are fabricated in the form of feed stock (wire or filament) that is formed into the required shape of a dental restoration using a fused deposition modeling machine such as FDM2000 available from Stratasys Inc., Eden Prairie, MN. The software used accounts for the anticipated shrinkage. The free-standing shaped article is then sintered to full density. This method can only be used for powder such as alumina or zirconia which is capable of isotropic shrinkage during sintering. U.S. Pat. No. 5,900,207 is directed to solid free form fabrication methods which is hereby incorporated by reference.

In another embodiment of the present invention, a slurry or paste of a polymer or ceramic powder is mixed with a carrier formed into a coping of a multi-layered final shape of a dental restoration using a machine similar to a fused deposition modeling machine. This machine emits or sprays beads of slurries as opposed to a fused deposition modeling machine which emits liquidfied thermoplastic materials. Examples of binder materials include curable organic materials such as mixtures of monomers or organic materials that are burned out prior to sintering. The shrinkage and setting of the materials are taken into account by oversizing the green body prior to sintering/curing.

In yet other embodiments of the present invention, other solid free-form fabrication techniques are used to make dental restorations from ceramic, glass-ceramic or composite materials.

In still another embodiment herein, SFF methods are used to provide only a skeleton of a dental restoration, e.g. a structure with interpenetrating porosity or a reticulated (cellular, honeycomb) body. This body is later infiltrated with "biological soup" containing cell cultures or peptides that can yield in-vitro grown materials similar to human tooth or bone tissues also known as biomimetic materials. For example, this infiltration media can contain biomimetically grown dental enamel crystals as described in U.S. Pat. No. 4,672,032 by Slavkin et al, which is hereby incorporated by reference. Another example of infiltration media is cultured periosteal cells as described in U.S. Pat. No. 5,700,289 to Breitbart et al.

In still yet another embodiment herein, rapid prototyping methods are used to form a "negative" or an impression of the tooth, teeth, or portion of the patient's mouth to be restored. As standard procedure, the dentist prepares the patient's tooth or teeth to be restored. Thereafter, the dentist takes an impression of the teeth. Alternatively, the dentist may scan the patient's teeth with a scanning device to obtain data that represents the shape of the patient's teeth. If an impression is taken, it is typically sent to a laboratory where a master die is made, or otherwise, the scanned data is sent to the laboratory or milling center for preparation of the restoration.

In accordance herein, if an impression is taken, it is scanned with a scanning device to obtain data representative of the shape of the impression. With the data obtained from the scanning of the impression or the scanning of the patient's mouth, a "negative" or shell material is prepared by a rapid prototyping process. The material used to prepare the shell is any material capable of withstanding the weight and force of a duplicate master or refractory model material including, but not limited to polymeric materials including, but not limited to waxes, nylons, plastics, rubber materials and other thermoplastic materials. Also, plaster and composite materials are other examples that may be useful herein. Examples of waxes include but are not limited to paraffin waxes, microcrystalline waxes, synthetic hydrocarbon waxes, oxidized polyethylene waxes and combinations of the foregoing. It s preferable that the wax has a modulus of elasticity of below about 10 GPa and more preferably below about 5 GPa. It is preferable that the wax have flow characteristics according to American Dental Association (ADA) Specification No. 4 for Type I and Type II waxes. At 45° C., the Type I and Type II waxes have a minimum flow percentage of 70% and a maximum flow percentage of 90%. If the shell is used as a wax pattern for casting or pressing restorations, it should burn out cleanly during burn-out procedures. It is important that waxes used are not too brittle and do not undergo dimensional changes under ambient conditions.

The aforementioned techniques and procedures discussed above in regard to the rapid prototyping of dental restorations apply hereto to the rapid prototyping of shells and are hereby incorporated by reference. The techniques used to form the shell may include three-dimensional printing, selective area laser deposition or selective laser sintering (SLS), electrophoretic deposition, robocasting, fused deposition modeling (FMD), laminated object manufacturing (LOM), stereolithography and photostereolithography. U.S. Pat. Nos. 5,340,656, 5,490,882, 5,204,055, 5,518,680, 5,490,962, 5,387,380, 5,700,289, 5,518,680, and 4,672,032 are directed to solid free-form fabrication methods and techniques and are hereby incorporated by reference.

The design of the shell is carried out by a CAD device which uses at least two inputs:

(1) the digital image taken optically directly from a mouth of the patient (optical impression) or created by digitizing the impression/die by contact or by an optical digitizer; and (2) a library of teeth shapes and forms. CAD devices assure both natural-like shape and proper function of the shell. Both optical and contact digitizers providing input (1) above are described in the literature and some of them are commercially available. The specific techniques may require additional software to build the shape according to the CAD file.

The data from the CAD file is input into the rapid prototyping device such as a fused deposition modeling machine. A continuous filament or rod of a polymeric material such as wax is introduced into a channel of a nozzle inside which the rod/filament is driven by a motor and associated rollers to move like a piston. The front end, near a nozzle tip, of this piston is heated to become melted. The rear end or solid portion of this piston pushes the melted portion forward to exit through the nozzle tip. The nozzle is translated under the control of a computer system in accordance with previously sliced CAD data to trace out a three-dimensional shell point by point and layer by layer. The CAD data may be modified to provide a shell having a thickness sufficient to withstand the weight and pressure of refractory die material that will be poured into the shell for fabrication of a model or die. The structure of the shell may be solid or reticulated. Preferably, the area of the shell closest to the internal surface of the shell exhibits a solid structure or form and the area further from the internal surface exhibits a reticulated or honey-comb structure. If the shell is to be used as a wax pattern for casting, it does not require bulking. It should have the dimensions of the restoration to be fabricated.

The shell obtained by rapid prototyping techniques is then used to fabricate a master model and/or a working die, both of which are used in the fabrication of dental restorations. Alternatively, as discussed, the shell can be used as a wax pattern for casting or pressing restorations. The technique used is commonly known as the lost-wax process. The shell, produced by techniques discussed herein, obviates the need for a dentist to send an impression to a dental laboratory, saving time and labor, and thereby expediting the process of manufacturing a dental restoration. After manufacture of the shell by rapid prototype techniques, a refractory die material or gypsum material is poured into the shell to provide a model or working die. A dental material, such as ceramic, composite, or alloy material, is applied or pressed onto the die to provide a dental restoration. Dental restorations manufactured using this process include, but are not limited to, orthodontic appliances, bridges, space maintainers, tooth replacement appliances, splints, crowns, partial crowns, dentures, posts, teeth, jackets, inlays, onlays, facing, veneers, facets, implants, abutments, cylinders, and connectors.

Figure 1:
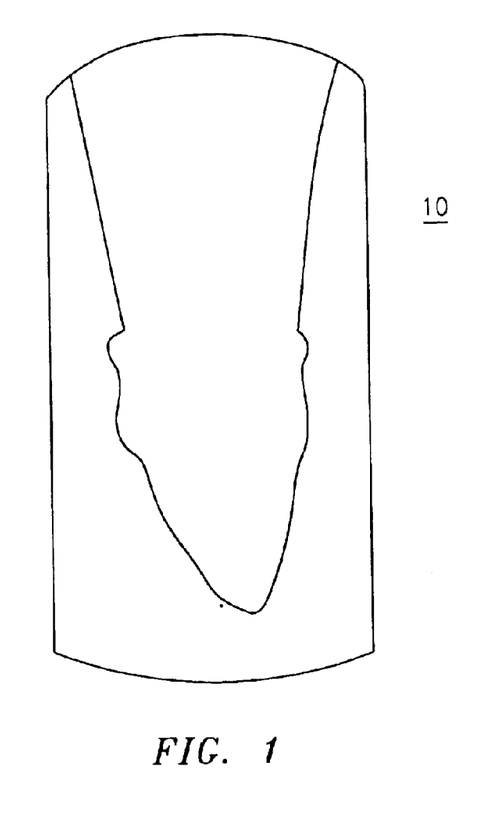
FIG. 1 is a cross-sectional view of a shell formed by rapid prototyping.
Figure 2:
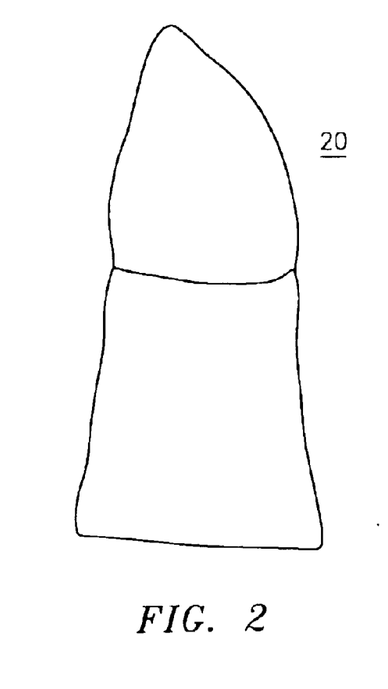
FIG. 2 is a elevational view of a model that has been formed from the shell of FIG. 1.
Figure 3:
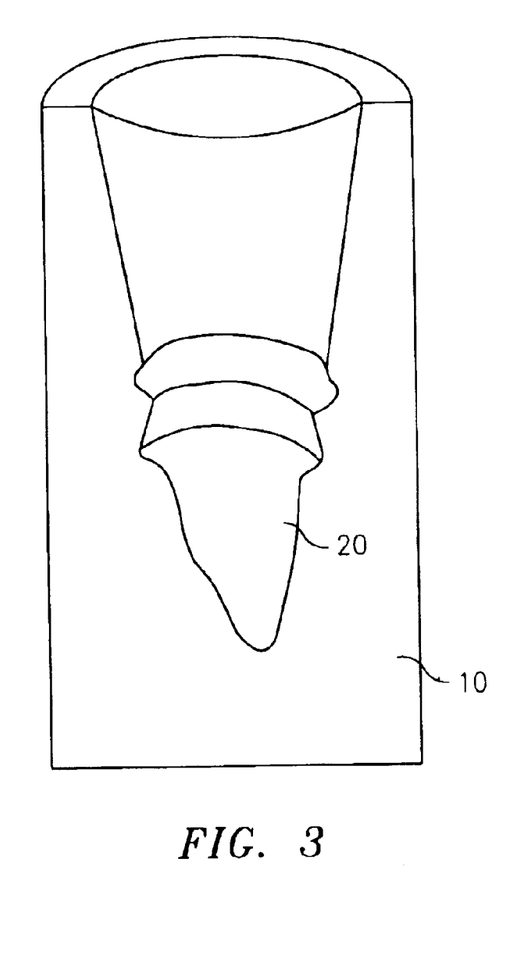
FIG. 3 is a cross-sectional view of a shell 10 with die 20 formed therein.
Figure 4:
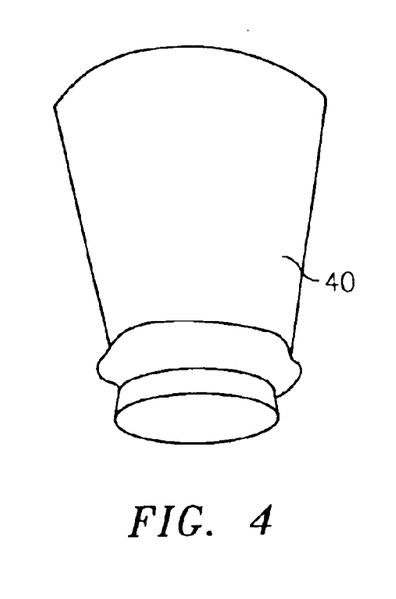
FIG. 4 is an elevational view of a plug for use in the shell of FIG. 3.
Figure 5:
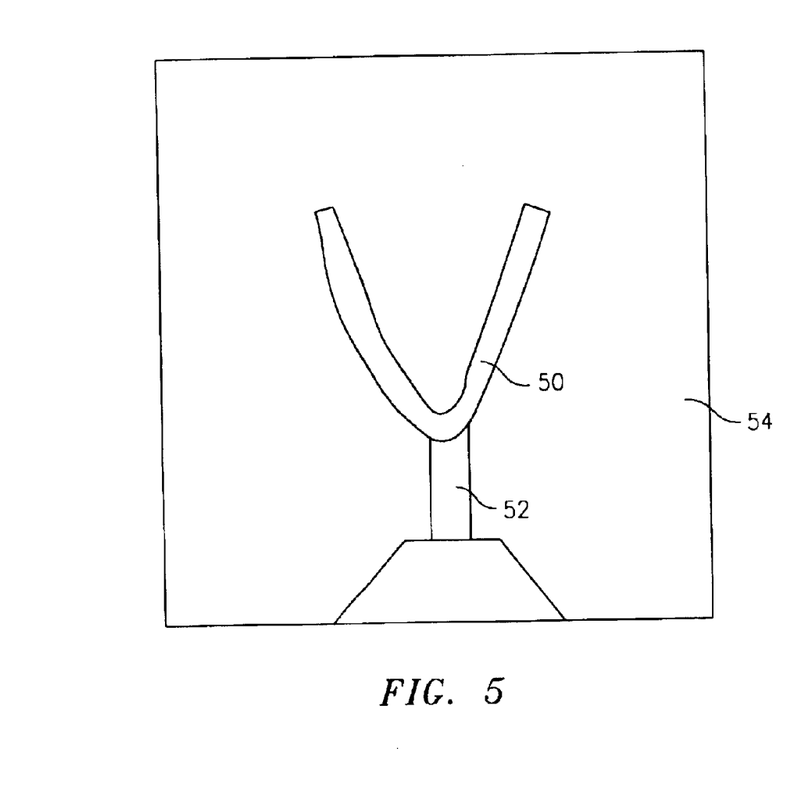
FIG. 5 is a cross-sectional view of a shell for use in the lost wax process.
Figure 6:
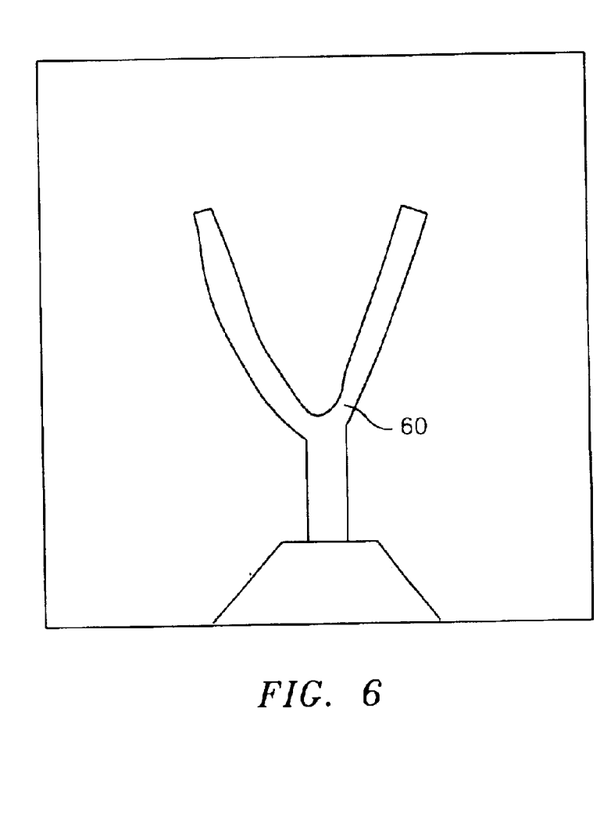
FIG. 6 is a cross-sectional view of a space made from the shell in FIG. 5.

Reference is made to FIGS. 1 through 6. FIG. 1 depicts a cross-sectional view of a shell 10 that has been formed by a rapid prototyping method as described herein. Shell 10 was formed from data retrieved by the dentist during the scanning procedure of the patient's tooth. The data was input into a rapid prototyping device to obtain shell 10. A die or model 20 shown in FIG. 2 was then prepared by filling shell 10 with refractory material known in the art. FIG. 3 is a cross-sectional view of shell 10 with die 20 formed therein. FIG. 4 shows a plug 40 that may be fabricated of a wax, plaster, plastic or rubber material. Plug 40 may be used to maintain the refractory material in place during setting after it has been poured into shell 10. FIG. 5 depicts a cross-sectional view of a shell 50 used in a lost wax process. Shell 50 is made using rapid prototyping techniques, based on information scanned from the patient's mouth or the impression taken from the patient's mouth. Shell 50 is shown attached to sprue 52 and is encased in investment material 54. During the burn-out procedure, shell 50 and sprue 52 are burned away, leaving a space 60 as shown in FIG. 6, for casting of metal or pressing of a ceramic.

In another embodiment herein, rapid prototyping techniques are used to fabricate master models and working dies or models that are used in the fabrication of dental restorations. Techniques and procedures discussed above in regard to the rapid prototyping of dental restorations and shells apply hereto to the rapid prototyping of master models and working models and are hereby incorporated by reference. The techniques used to form the models and dies may include three-dimensional printing, selective area laser deposition or selective laser sintering (SLS), electrophoretic deposition, robocasting, fused deposition modeling (FMD), laminated object manufacturing (LOM), stereolithography and photostereolithography. U.S. Pat. Nos. 5,340,656, 5,490,882, 5,204,055, 5,518,680, 5,490,962, 5,387,380, 5,700,289, 5,518,680, and 4,672,032 are directed to solid free-form fabrication methods and techniques and are hereby incorporated by reference.

Similar to the aforementioned techniques used to form shells and dental restorations, data received from scanning the patient's mouth or the impression of the patient's mouth is used to fabricate models using solid free-form fabrication methods. Materials useful for the manufacture of models include investment materials. Typical investment materials include gypsum for low temperature applications, and a refractory filler, such as silica in the form of cristobalite, quartz, or a mixture of the two, leucite, zirconia, hafnia, zircon, alumina, magnesia, zircon, aluminosilicate, cordierite, mica, silicon nitride, silicon carbide, silica-alumina-nitrides, mullite, garnet, or mixtures thereof, in combination with a binder, for high temperature applications. Binders may include but are not limited to inorganic and organic binders, or mixtures thereof. Organic binders include, but are not limited to, polyvinyl pyrrolidine, polyvinyl alcohol, polyvinyl acetate, polyvinyl chloride, polyvinyl butryal and polystyrene, or mixtures thereof. Inorganic binders include, but are not limited to, magnesium oxide, ammonium phosphate, colloidal silica, calcium sulfate, magnesium phosphate, alkaline silicates, silica hydrosol, colloidal clays, or mixtures thereof. The investment material is fed to the solid free-form apparatus which interprets the scanned data and produces a three-dimensional model with the investment material.

Alternatively, the model may be formed of a thermoplastic material as described above for the use of shells, and the wax model may be duplicated using standard techniques.

For all purposes and materials used herein, the hardening or curing step may involve gelation, heating, cooling, or the application to promote the integrity of the solid free-form structure.

The following examples illustrate the practice of the present invention.

Example 1

Filament is prepared from Investment Casting Wax (ICW06, Stratasys) and thermoplastic ABS (P400, Stratasys) and equiaxed alumina powder of 5 to 10 microns particle size. The binder content is about 30 volume percent.

Using a CAD/CAM device and digitizer manufactured by CAD/CAM Ventures (Irving, TX), the model of a tooth preparation is digitized and the obtained CAD file is used in conjunction with an FDM2000 fused deposition modeling machine available from Stratasys Inc. (Eden Prairie, MN). Using the filament containing equiaxed alumina powder in a thermoplastic matrix, single and multiunit dental restorations are formed and then subjected to binder-removal and soft-sintering cycles. The resulting porous preforms are infiltrated with glass using materials supplied by Vita Zahnfabrick (Bad Sackingen, Germany) and glass infiltration techniques used for Vita In-Ceram Alumina restorations.

Example 2

The same CAD file as used in Example 1 is used in conjunction with a three-dimensional printing machine such as the Z402 System available from Z Corporation (MA) to print on ceramic powder and on metal powder separately. The same powder-binder mixture used above is used herein as the powder layer. A binder mixed with finely dispersed pigments is printed on the powder layer. Successive layers are deposited to form a dental restoration based on the CAD file. After the restoration is fully formed, the binder is burned out and glass is then infiltrated into the interstices. The pigment is retained in interstitial sites between the alumina particles to impart a shade to the composite.

Example 3

Using a CAD/CAM device and digitizer manufactured by CAD/CAM Ventures (Irving, TX), the model of a tooth preparation is digitized and the obtained CAD file is used to manufacture a shell. The CAD file is modified to provide a thickness in the shell great enough to support and withstand the refractory materials. The thickness of the shell varies from about 0.5 to about 10 mm in thickness. The shell produced is thinner near the margin and thicker near the apex. This information is fed into a computerized liquid wax dispensing machine. A green injection wax available from Romanoff Inc is injected into the machine. The wax is delivered as tiny beads in liquid state that solidify shortly after dispensing. The internal surface of the shell is smooth. The support structure of the shell is in the form of a solid or void-containing structure, such as a honeycomb structure. Polyvest refractory material available from WhipMix corporation is poured into the shell and sets. After setting, a duplicate refractory die is retrieved and used for further processing of materials.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A process for manufacturing a dental restoration comprising:

manufacturing a shell by rapid prototyping, wherein the shell is a replica of a coping, wherein the coping is in the shape of denture teeth, a bridge, crown, tooth replacement appliance, denture, post, jacket, inlay, onlay, facing, veneer, facet, splint, partial crown, cylinder, pin, or connector;

covering the shell with refractory material;

burning out the shell to provide a space in the refractory material; and filling the space with ceramic, metal or composite material to form the dental restoration.

2. The process of claim 1 wherein the ceramic comprises alumina, zirconia, apatite, fluoroapatite, hydroxyapatite or a mixture thereof.

3. The process of claim 1 wherein the composite material comprises a polymeric matrix material having particulate or fiber filled components.

4. The process of claim 3 wherein the polymeric matrix material comprises polyamides, polyesters, polyolefins, polyimides, polyarylates, polyurethanes, vinyl esters, epoxy-based materials, styrenes, styrene acrylonitriles, ABS polymers, polysulfones, polyacetals, polycarbonates, polyphenylene sulfides, or mixtures thereof.

5. The process of claim 3 wherein the polymeric matrix material comprises acrylic or methacrylic monomers or a mixture thereof.

6. The process of claim 3 wherein the polymeric matrix material comprises the condensation product of bisphenol A and glycidyl methacrylate, 2,2'-bis[4(3-methacryloxy-2-hydroxy propoxy)-phenyl]-propane ("BIS-GMA"), polyurethane dimethacrylates ("PUDMA"), triethylene glycol dimethacrylate ("TEGDMA"), polyethylene glycol dimethacrylate ("PEGDMA"), polycarbonate dimethacrylate ("PCDMA"), ethoxylated bisphenol A dimethacrylate ("EBPADMA") or a mixture thereof.

7. The process of claim 3 wherein the polymeric matrix material further comprises one or more of a polymerization initiator, polymerization accelerator, ultraviolet light absorber, fluorescent whitening agent, and an anti-oxidant.

8. The process of claim 7 wherein the polymerization initiator comprises camphorquinone (CQ), trimethyl benzoyl phosphine oxide (TPO), benzoyl peroxide, or 1,1'-azobis(cyclohexanecarbo-nitrile).

9. The process of claim 3 wherein the fiber component comprises ceramic, glass, carbon, graphite, polyaramid, polyester, polyamide, or a mixture thereof.

10. The process of claim 3 wherein the particulate component comprises silica, silicate glass, quartz, barium silicate, barium sulfate, barium molybdate, barium methacrylate, barium yttrium alkoxy ($Ba_2Y(OR)_x$), strontium silicate, barium borosilicate, strontium borosilicate, borosilicate, lithium silicate, amorphous silica, ammoniated or deammoniated calcium phosphate, alumina, zirconia, tin oxide, tantalum oxide, niobium oxide, titania or a mixture thereof.

* * * * *